US008889393B2

(12) United States Patent
Sjöblom et al.

(10) Patent No.: US 8,889,393 B2
(45) Date of Patent: Nov. 18, 2014

(54) METHOD AND KIT FOR SEQUENTIAL ISOLATION OF NUCLEOTIDE SPECIES FROM A SAMPLE

(75) Inventors: Tobias Sjöblom, Uppsala (SE); Lucy Mathot, Uppsala (SE)

(73) Assignee: ExScale Biospecimen Solutions AB, Uppsala (SE)

( * ) Notice: Subject to any disclaimer, the term of this patent is extended or adjusted under 35 U.S.C. 154(b) by 0 days.

(21) Appl. No.: 13/704,739

(22) PCT Filed: Jun. 27, 2011

(86) PCT No.: PCT/SE2011/050848
§ 371 (c)(1),
(2), (4) Date: Mar. 7, 2013

(87) PCT Pub. No.: WO2012/002887
PCT Pub. Date: Jan. 5, 2012

(65) Prior Publication Data
US 2013/0164819 A1 Jun. 27, 2013

(30) Foreign Application Priority Data

Jun. 29, 2010 (SE) ...................................... 1000701
Nov. 22, 2010 (SE) ...................................... 1100480

(51) Int. Cl.
- C12N 9/16 (2006.01)
- A61K 38/00 (2006.01)
- C12N 15/10 (2006.01)
- C07H 21/00 (2006.01)

(52) U.S. Cl.
CPC ............ *C12N 15/1006* (2013.01); *C07H 21/00* (2013.01)
USPC ...................................................... 435/196

(58) Field of Classification Search
None
See application file for complete search history.

(56) References Cited

U.S. PATENT DOCUMENTS

| 5,990,301 | A | 11/1999 | Colpan et al. |
| 6,180,778 | B1 | 1/2001 | Bastian et al. |
| 6,355,792 | B1 * | 3/2002 | Michelsen et al. ........... 536/25.4 |
| 6,946,250 | B2 | 9/2005 | Bastian et al. |
| 7,074,916 | B2 | 7/2006 | Bastian et al. |
| 7,655,792 | B2 | 2/2010 | Takkellapati et al. |
| 7,655,793 | B2 | 2/2010 | Herzer et al. |
| 7,655,794 | B2 | 2/2010 | Takkellapati et al. |
| 2003/0138828 | A1 | 7/2003 | Bost et al. |
| 2005/0239068 | A1 | 10/2005 | Bosnes |
| 2009/0234112 | A1 | 9/2009 | Hillebrand |
| 2010/0292446 | A1 | 11/2010 | Takkellapati et al. |

FOREIGN PATENT DOCUMENTS

| DE | 10358137 A1 | 7/2005 |
| DE | 102006031764 A1 | 10/2008 |
| WO | 96/18731 A2 | 6/1996 |
| WO | 2003/046146 A2 | 6/2003 |
| WO | 2004/003231 A2 | 1/2004 |
| WO | 2004/108925 A1 | 12/2004 |
| WO | 2008/003776 A2 | 1/2008 |
| WO | WO 2009/134652 * | 5/2009 ............. C12N 15/10 |
| WO | 2009/134652 A2 | 11/2009 |

OTHER PUBLICATIONS

Mahalanabis et al. "Cell lysis and DNA extraction of gram-positive and gram-negative bacteria from whole blood in a disposable microfluid chip" 2009 Lab Chip 9 281102817.*
Okunbowa et al. "Mechanical lysis of *Candida* cells for crude protein and enzymatic activity estimation comparison of three methods" 2007 World Journal of Medical Sciences 2(2) 101-104.*
Taylor et al. "Application of magnetite and silica magnetite composites to the isolation of genomic DNA" 2000 Journal of Chromatography A 890 159-166.*
Ambion Technical Resoursce 2007 DNase I Demystified.*
Sepmag, Precision Magnetophoresis beyond magnetic separation, Estapor, Dec. 20, 2010.
Mathot et al, Efficient and Scalable Serial Extraction of DNA and RNA from frozen tissue samples, Chem. Comm., 47(1): 547-549 (online Nov. 23, 2010).
Merck, MagPrep, Magnetic Particles with Unique Features, Estapor, May 24, 2010.
Hourfar et al, High-Throughput Purification of Viral RNA Based on Novel Aqueous Chemistry for Nucleic Acid Isolation, Clinical Chemistry, 51:7, 2005, p. 1217-1222.
Merck, Nucleic Acid Technology, Estapor, Dec. 20, 2010.
Berensmeier, Magnetic particles for the separation and purification of nucleic acids, Appl., Microbiol., Biotechnol, 2006, 73:495-504.

(Continued)

*Primary Examiner* — Suzanne M Noakes
*Assistant Examiner* — Gerard Lacourciere
(74) *Attorney, Agent, or Firm* — Porter Wright Morris & Arthur LLP

(57) ABSTRACT

The invention provides a process and kit for serial isolation of DNA and RNA from the same sample. First, a siliceous solid support with preferential affinity for DNA over RNA is used to capture DNA in a lysate of a sample. Next, a siliceous solid support with similar affinity for RNA and DNA is used to capture RNA from the same lysate. The respective solid supports are recovered independent of each other, washed, and their bound nucleotide species are eluted. The invention further provides DNA and RNA prepared using the process in a minimal number of steps employing a minimal number of reagents. As the invention yields DNA and RNA of high quality and is amenable to automation, the invention may be used widely in the healthcare and pharmaceutical industries.

31 Claims, 7 Drawing Sheets

(56) References Cited

OTHER PUBLICATIONS

Tseng et al, Enhanced purification of plasmid DNA using Q-Sepharose by modulation of alcohol concentrations, Journal of Chromatography B, Biomedical Sciences and Applications, 791(1-2): 263-272 (2003).

Mathot et al, Automated serial extraction of DNA and RNA from biobanked tissue specimens, BMC Biotechnology, 13:66 (6 pages) (Aug. 2013).

Extended European Search Report form the corresponding European Application No1 11801242.6, dated Feb. 25, 2014.

* cited by examiner

A

B

METHOD AND KIT FOR SEQUENTIAL ISOLATION OF NUCLEOTIDE SPECIES FROM A SAMPLE

TECHNICAL FIELD

The present invention relates to the field of molecular genetics. Particularly, the present invention relates to a unique solution and methods of use thereof for separating and purifying biological materials. More particularly, the present invention relates to serial purification of DNA and RNA from the same sample, in which two silicaceous materials with different selectivity for binding DNA and RNA are used to bind the target DNA or RNA. The present invention provides highly purified DNA and RNA that may be used widely, especially in medical and biological research, healthcare and pharmaceutical industries.

BACKGROUND

A method for separating and/or preparing highly purified target substances from different biomaterials is difficult because natural biomaterials, such as tissue, cell, blood, bacteria, are complicated mixtures. However, isolation and purification of target substances from such biomaterials are often needed in diagnostics, biomedical research, and/or other applications. For example, in a natural state, deoxyribonucleic acids (DNAs) and ribonucleic acids (RNAs) are often mixed with other substances, such as proteins, lipids and carbohydrates; isolating and purifying these DNA and RNA molecules containing a target gene or a target gene transcript, respectively, is often necessary for investigating the gene.

With the fast advances in molecular biology and other related fields, there is a need for a new method for consecutive DNA and RNA isolation and purification from the same sample that is safe, effective, and suitable for automation and industrialization. It has been reported that certain silicon-containing materials can absorb target substances in the presence of binding agents or binding enhancers. The target substances can then be purified by being eluted from the silicon carrier after the impurities are eliminated. U.S. Pat. No. 6,218,531 discloses a method for isolating RNAs from lysed biomaterials with silicon binding carrier in the presence of chaotropic reagents.

The underlying mechanism for these nucleic acid isolation and purification methods is that silicon-containing materials can reversibly bind DNA, RNA and hybrid molecules of DNA and RNA in the presence of binding reagents. Some common chaotropic binding reagents include NaI, urea, guanidine hydrochloride, $NaClO_4$, and KBr. Alcohol, such as 100% ethanol, is also a commonly used binding reagent for nucleic acid purification (see the background of European Pat. App. No. 0512676 A1 and U.S. Pat. No. 5,783,686).

Procedures for purification of nucleic acids using silicaceous matrices frequently involve washes of the support with bound nucleic acids in alcohol containing solutions to remove impurities. Preferably, a simple and robust process for nucleic acid purification is based on matrices where bound nucleic acids can be washed in non-alcohol containing solutions. In U.S. Pat. No. 6,355,792, a method for isolating and purifying nucleic acids comprising a solid carrier exposing hydroxyl groups where the nucleic acids are bound to the carrier material in a solution containing chaotropic agents in the acidic pH range, and eluted in the alkaline pH range is disclosed.

The binding of small RNA molecules, such as miRNA, onto silicaceous materials can be enhanced by addition of acetone or acetonitrile to the lysis buffer (U.S. Pat. App. No. 2009/0143570).

Procedures for sequential purification of DNA and RNA from the same sample have been devised. For example, WO2004/108925 discloses a method based on different affinities of RNA and DNA to a silicaceous matrix under different concentrations of ethanol in the binding buffer.

The recovery of RNA from complex mixtures with silica matrices may be adversely affected through competition for binding with DNA present in such mixtures. To alleviate these problems, it has been known to use a matrix for selective removal of DNA prior to binding RNA to enhance binding of the latter.

It should be noticed that, while using silicaceous materials as reversible absorbing materials for nucleic acids, the use of alcohols in wash buffers may result in alcohol contamination of the eluted end product. Such contamination may be detrimental to the performance of the end product in downstream processes.

Therefore, there is a need to provide a new, effective process for the recovery of different nucleic acid species from the same sample and where impurities can be removed by washing in aqueous buffer without alcohols, and the process is amenable to automation.

SUMMARY

According to one aspect of the invention, there is provided a method of sequentially isolating different nucleic acid species, such as DNA and RNA, from a biological sample. The method comprises the steps of:

in a first binding step, selectively binding a first nucleic acid species to a first solid phase by contacting the biological sample with the first solid phase that selectively binds the first nucleic acid species;

separating the first solid phase with the bound first nucleic acid species from an unbound portion of the biological sample;

in a second binding step, selectively binding a second nucleic acid species to a second solid phase, different from the first solid phase, by contacting an unbound portion of the biological sample with the second solid phase that binds the first and second nucleic acid species;

enzymatic digestion of the first nucleic acid species bound to the second solid phase; and isolating the second nucleic acid species from the second solid phase.

According another aspect of the invention, there is provided a kit comprising a combined lysis and nucleic acid binding buffer, a first solid phase that selectively binds DNA in the nucleic acid binding buffer, a second solid phase that is different from the first solid phase and binds RNA and DNA in the nucleic acid binding buffer, a wash buffer, a wash buffer for digestion of DNA, and an elution buffer. The kit may also comprise a substance to enhance binding of RNA to the second solid phase.

DETAILED DESCRIPTION OF THE INVENTION

The methods of the present invention can be used to consecutively isolate DNA and RNA from any one of a number of different sources, including biological material such as cells or tissue. The description of the present method, below, is directed to the isolation of DNA and RNA from biological material, as such material is the most difficult of all of the sources described above from which to isolate intact, functional DNA and RNA. This description is not, however, intended to limit the scope of the present invention to the isolation of RNA from such sources alone, as the present method can be applied to materials obtained using methods other than those described below.

Figure 1:
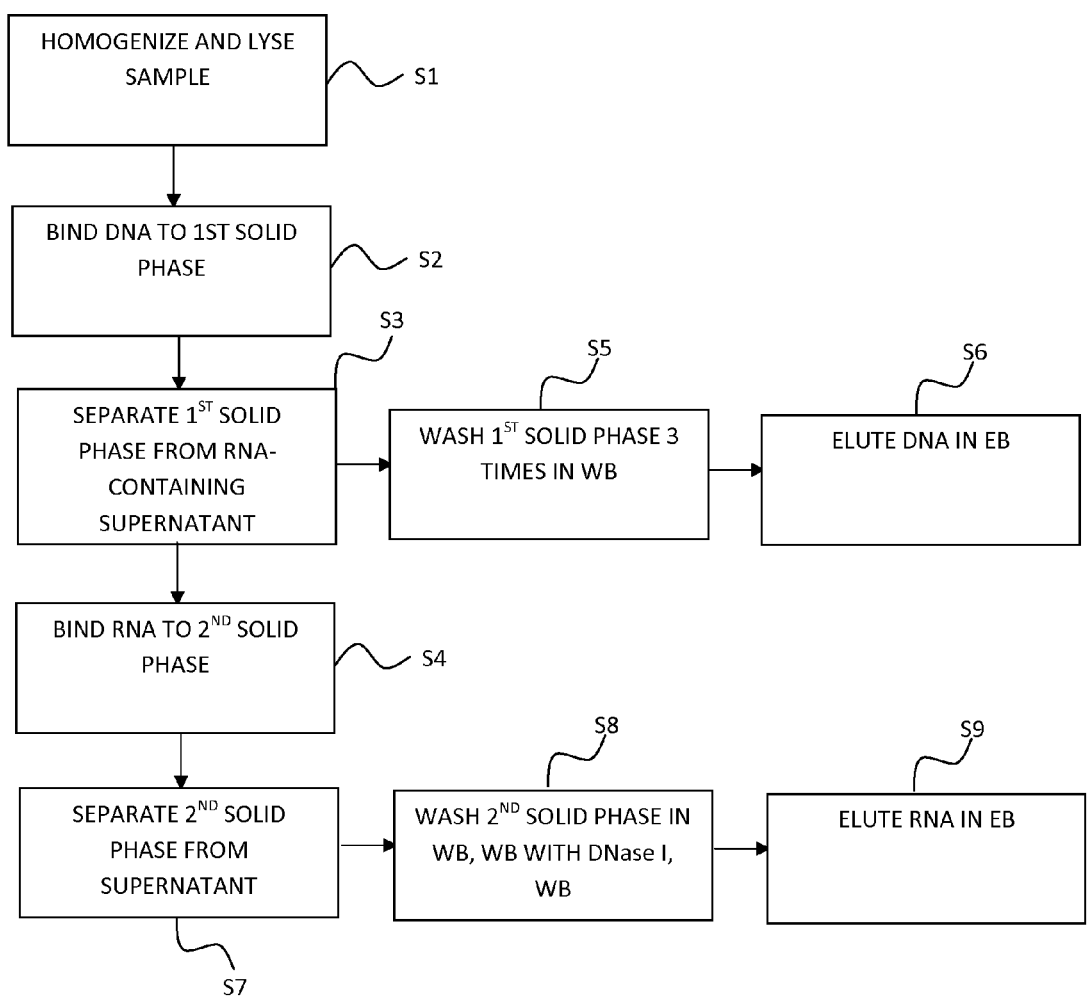
FIG. 1 is a flow diagram of a method according to the present invention for serially isolating DNA and RNA, wherein: (S1) biological material is homogenized and lysed; (S2) the lysate is incubated with magnetic particles that preferentially bind DNA rather than RNA; (S3) the magnetic particles with bound DNA are separated from the RNA-containing supernatant; (S5) the magnetic beads are washed to remove impurities; (S6) the bound DNA is eluted; (S4) magnetic particles that bind RNA are incubated with the resulting lysate post DNA recovery; (S7) the magnetic particles with bound RNA are separated from the supernatant; (S8) magnetic particles with bound RNA are washed to remove impurities; and (S9) the RNA is eluted. Lysis Buffer (LB): 7 M Guanidine HCl, 50 mM Tris pH 7, 0.95 mg/ml Proteinase K, 2% Tween 20; Wash Buffer (WB): 10 mM Tris-HCl pH 6.5; Elution Buffer (EB): 10 mM Tris-HCl pH 8.6, 1 mM EDTA).

FIG. 1 is a flow diagram illustrating a method of sequentially isolating different nucleic acid species, such as DNA and RNA, from a biological sample according to an aspect of the embodiments. The method comprises the steps of:

in a first binding step, selectively binding a first nucleic acid species to a first solid phase by contacting the biological sample with the first solid phase that selectively binds the first nucleic acid species;

separating, the first solid phase with the bound first nucleic acid species from an unbound portion of the biological sample;

in a second binding step, preferential binding a second nucleic acid species to a second solid phase, different from the first solid phase, by contacting an unbound portion of the biological sample with the second solid phase that binds the first and second nucleic acid species;

enzymatic digestion of the first nucleic acid species bound to the second solid phase; and isolating the second nucleic acid species from the second solid phase.

In a particular embodiment, the method comprises:

step S1: lysis, homogenization and protease digestion of the tissue in a lysis buffer thereby generating a lysate;

step S2: addition of a first solid support to the lysate, binding of the first nucleotide species to the first solid support, and step S3: retrieval of the first solid support with first nucleotide species bound onto it;

step S5: washing of the first solid support with the first nucleotide species bound onto it;

step S6: elution of the first nucleic acid species from the first solid support;

step S4: addition of a second solid support to the lysate, binding of the second nucleotide species to the second solid support, and step S7: retrieval of the second solid support with the second nucleotide species bound onto it;

step S8: washing of the second solid support with the second nucleotide species bound onto it; and step S9: elution of the second nucleic acid species from the second solid support.

In an embodiment, the lysis buffer, the wash buffer used for washing the first and second solid support and the elution buffer used for elution of the first and second solid support are devoid of any alcohols. Thus, in a preferred embodiment none of the buffers of the embodiments comprise ethanol or any other alcohol.

In one embodiment of the method, the first nucleic acid species is deoxyribonucleic acid (DNA) and the second nucleic acid species is ribonucleic acid (RNA). In a further embodiment, the first solid support preferentially/selectively binds DNA over RNA when contacted with a mixture containing DNA and RNA. In still a further embodiment, the second solid support has greater or equal affinity for RNA than for DNA when contacted with a mixture containing DNA and RNA.

In another embodiment of said method, the first nucleic acid species is ribonucleic acid (RNA) and the second nucleic acid species is deoxyribonucleic acid (DNA). In such an embodiment, the first solid support preferentially binds RNA over DNA. In still a further embodiment, the second solid support has greater or equal affinity for DNA than for RNA.

The first and/or second solid support may be composed of magnetic or superparamagnetic particles. In one embodiment, the first and/or second solid support is composed of SiOH-coated magnetite crystals in the size range 100-200 nm with >90% magnetite content. In another embodiment, the first solid support is constituted by MagPrep Silica HS beads. In another embodiment, the second solid support is constituted by MagPrep Basic Silica beads. In a further embodiment, the first solid support is constituted by MagPrep Silica HS beads and the second solid support is constituted by MagPrep Basic Silica beads.

The biological sample may for example be selected from tissue, fresh or frozen cells of any organism including a mammal, tissues embedded in freeze protection resin such as OCT compound, fresh or frozen cell pellets from blood or bone marrow, blood plasma or buffy coat and rehydrated sections of formaldehyde-fixed and paraffin-embedded mammalian tissue.

The method of the present invention uses chaotropic salts at the lysis stage to ensure the biological material is sufficiently disrupted to release DNA and RNA contained in the sample into the lysis solution, and to inactivate enzymes likely to degrade the DNA such as DNases, or degrade the RNA such as RNases. Such chaotropic agents, in association with detergents, such as Tween-20, also serve to disrupt protein interactions with nucleic acids, thereby further releasing the nucleic acids in solution. In association with proteases, such as Proteinase K, release of nucleic acids can be further enhanced. Mild heating and mechanical grinding, such as is achieved by shaking of the lysate in presence of a steel ball, can further enhance release of nucleic acids from tissues. Chaotropic salts are suitable binding enhancers to include in the binding mixture placed in contact with a silicaceous material to form a complex of nucleic acid and the silica matrix in the further processing steps of some of the aspects of the methods of the present invention. Chaotropic salts include guanidine hydrochloride, guanidine thiocyanate, sodium iodide, sodium perchlorate, and sodium trichloroacetate. Preferred are the guanidinium salts, more preferably guanidine hydrochloride or guanidine thiocyanate, but most preferably guanidine hydrochloride.

The preferred embodiments of the methods of the present invention use a silica matrix to first isolate DNA from a lysate produced according to the pre-treatment methods of this invention. The silica matrix used to isolate DNA in the preferred methods is preferably a silica matrix in form of a magnetic particle. The most preferred silica matrix is a magnetic particle that selectively binds DNA rather than RNA, such as MagPrep Silica HS beads (Merck Estapor). Only the most preferred silica matrix and its use in the methods of the present invention are specifically described below. However, the present invention is not limited to the particular form of silica matrix discussed below.

In the first binding step S1 of FIG. 1, a biological sample may be lysed in 7 M guanidine HCl, 50 mM Tris pH 7, 2% Tween 20. The biological sample may be ground in lysis buffer using a steel ball and rotary shaking at 55-65° C. for 15-45 min. The lysate may also comprise Proteinase K at a final concentration of 1 mg/ml and may be incubated at 37-65° C., such as 55-65° C., for 15-45 min to remove protein. In a particular embodiment, grinding and incubation can be performed at 58° C. for 35 min.

Binding of DNA in the present method is accomplished by contacting the lysate with the preferred silica matrix at ambient temperature for more than 30 seconds in step S2. In a preferred embodiment, the contact time is in the range 1-15 min. After binding of DNA to the preferred silica matrix, the matrix is retained by centrifugation, filtration, sedimentation, or application of a magnetic field in step S3. Most preferably, the complex of silica matrix and DNA is retained by a magnetic field applied from below or from the side of the vessel containing the mixture of lysate and matrix. In one preferred embodiment, several independent lysate and matrix mixtures are contained in the wells of a standard plate, such as a 96- or 384-well plate, and the magnetic field is applied by bringing into proximity a plate with magnetic posts or rings surrounding the vessels by manual or automatic means.

While the supernatant is transferred into a novel vessel for subsequent RNA capture, the complex of silica matrix and DNA is retained in the first vessel for washes in step S5 and elution in step S6. The wash solutions used in the washing steps of the methods of DNA isolation of the present invention are all done using wash solutions designed to remove material from the silica matrix without removing the DNA bound thereto. The wash solutions used in the present method preferably comprise a salt and buffer at slightly acidic pH in the range 6-7. The salt is preferably in the form of a buffer, and most preferably in the form of a Tris buffer, such as Tris-HCl, at pH 6.5. In a preferred embodiment, the complex of silica matrix and DNA are washed three times in wash solution while retained in a magnetic field.

The elution solution used to elute the DNA from the silica matrix complex in the elution step of the present method is preferably an aqueous solution of low ionic strength, more preferably a low ionic strength buffer in the basic pH range at which the nucleic acid material is stable and substantially intact. Any aqueous solution with an ionic strength at or lower than TE buffer (i.e. 10 mM Tris-HCl, 1 mM ethylenediaminetetraacetic acid (EDTA), pH 8.0) is suitable for use in the elution steps of the present methods, but the elution solution is preferable buffered to a pH between 8.0 and 10.0. TE Buffers at pH 8.6 or 9 are particularly preferred elution solutions for use in the present invention. Other elution solutions suitable for use in the methods of this invention will be readily apparent to one skilled in this art. In a particular embodiment, the elution may be performed in 10 mM Tris-HCl pH 8.6, 1 mM EDTA with mixing up to 20 times and heating to 55-65° C., such as 58° C., for 5-10 min, such as 10 min.

The DNA eluted from the silicaceous magnetic particles by the method of the present invention is suitable, without further isolation, for analysis or further processing by molecular biological procedures. The eluted DNA can be sequenced, analyzed directly using gel electrophoresis, and used in polymerase chain reactions. Thus, the methods of the invention can be applied as part of methods, based on analysis of DNA, for, among other things, diagnosing diseases; identifying pathogens; testing foods, cosmetics, blood or blood products, or other products for contamination by pathogens; forensic testing; paternity testing; and sex identification of fetuses or embryos.

In the RNA binding step of the present invention, it is essential that the DNA amount has been reduced in the lysate since residual DNA competes with RNA for binding to many silica matrices. In the most preferred embodiment, the reduction of DNA content is achieved by capture on a silica matrix in form of a magnetic particle as described above and retrieval of the remaining lysate. To the remaining lysate, silica matrices in form of magnetic particles with affinity for RNA given the conditions in the lysate are added in a preferred embodiment in step S4. In the most preferred embodiment, silicaceous magnetic particles which bind RNA with equal or better affinity than DNA in the conditions of the lysate, such as MagPrep Silica Basic particles (Merck Estapor) are incubated with the lysate. Binding of RNA and residual DNA in the present method is accomplished by contacting the lysate with the preferred silica matrix at ambient temperature for more than 30 seconds. In a preferred embodiment, the contact time is in the range 1-15 min. In the most preferred embodiment, the contact time is 15 min. Only the most preferred silica matrix and its use in the methods of the present invention are specifically described below. However, the present invention is not limited to the particular form of silica matrix discussed below.

After binding of RNA to the preferred silica matrix, the matrix is retained by centrifugation, filtration, sedimentation, or application of a magnetic field in step S7. Most preferably, the complex of silica matrix and RNA is retained a magnetic field applied from below or from the side of the vessel containing the mixture of lysate and matrix. In one preferred embodiment, several independent lysate and matrix mixtures are contained in the wells of a standard plate, such as a 96- or 384-well plate, and the magnetic field is applied by bringing into proximity a plate with magnetic posts or rings surrounding the vessels by manual or automatic means.

The wash solutions used in the washing steps of the methods of RNA isolation of the present invention in step S8 are all done using wash solutions designed to remove material, including DNA, from the silica matrix without removing the RNA bound thereto. The wash solutions used in the present method preferably comprise a salt and buffer at slightly acidic pH in the range 6-7. The salt is preferably in the form of a buffer, and most preferably in the form of a Tris buffer, such as Tris-HCl, at pH 6.5. In a preferred embodiment, the complexes of silica matrix and RNA are washed three times in wash solution while retained in a magnetic field. To remove residual DNA, DNase treatment is preferably done by incubating the silica matrix complexed with RNA with wash solution containing 1-2 U, such as 1 U, DNase I after at least one wash step. After washing in the DNase containing wash solution, the complexes are preferably washed once in wash solution without DNase to ensure that the eluted product does not contain DNase. In the most preferred embodiment, the complexes of silica matrix and RNA are washed once in Tris-HCl pH 6.5, then once in Tris-HCl pH 6.5 containing 1-2 U, such as 1 U, DNase I, and finally once in Tris-HCl pH 6.5.

The elution solution used to elute the RNA from the silica matrix complex in the elution step S9 of the present method is preferably an aqueous solution of low ionic strength, more preferably water or a low ionic strength buffer in the basic pH range at which the nucleic acid material is stable and substantially intact. Any aqueous solution with an ionic strength at or lower than TE buffer (i.e. 10 mM Tris-HCl, 1 mM ethylenediamine-tetraacetic acid (EDTA), pH 8.0) is suitable for use in the elution steps of the present methods, but the elution solution is preferable buffered to a pH between 8.0 and 10.0. TE Buffers at pH 8.6 or 9 are particularly preferred elution solutions for use in the present invention. Other elution solutions suitable for use in the methods of this invention will be readily apparent to one skilled in this art. In a particular embodiment elution is performed in 10 mM Tris-HCl pH 8.6, 1 mM EDTA.

The RNA eluted from the silicaceous magnetic particles by the method of the present invention is suitable, without further isolation, for analysis or further processing by molecular biological procedures. The eluted RNA can be sequenced or analyzed directly using gel electrophoresis. The eluted RNA can also be used for reverse transcription with a reverse transcriptase polymerase chain reaction (RT-PCR). Thus, the methods of the invention can be applied as part of methods, based on analysis of RNA, for, among other things, diagnosing diseases; identifying pathogens; testing foods, cosmetics, blood or blood products, or other products for contamination by pathogens; forensic testing; paternity testing; and sex identification of fetuses or embryos.

The method illustrated in FIG. 1 shows the steps in sequential order. However, the sequential DNA and RNA extraction can be performed at least partly in parallel. For instance, steps S5 and S6 can be performed at least partly in parallel with steps S8 and S9. Thus, the washing of the first solid phase and the second solid phase can be performed at least partly in parallel and the elution of the DNA from the first solid phase and the elution of the RNA from the second solid phase can be performed at least partly in parallel.

According another aspect of the embodiments, there is provided a kit comprising a combined lysis and nucleic acid binding buffer, a first solid phase that selectively binds DNA in the nucleic acid binding buffer, a second solid phase that is different from the first solid phase and binds RNA and DNA in the nucleic acid binding buffer, a wash buffer, a wash buffer for digestion of DNA, and an elution buffer. The kit may also comprise a substance to enhance binding of RNA to the second solid phase. The wash buffer for digestion of DNA is preferably the previously described wash buffer complemented with a DNase, preferably DNase I.

The first solid phase, i.e. the DNA-binding beads, are preferably Magprep Silica HS beads that are preferably diluted 1 in 3 in lysis buffer from a stock solution of 50 mg/ml to get in total 833.3 mg beads at a volume of 50 mL. Correspondingly, the second solid phase, i.e. the RNA-binding beads, are preferably Magprep Silica Basic beads that are preferably diluted 1 in 3 in lysis buffer from a stock solution of 50 mg/ml to get in total 833.3 mg beads at a volume of 50 mL. The kit preferably also comprises lysis buffer with Proteinase K, preferably in the form of 7 M Guanidine HCl, 50 mM Tris, 2% Tween (pH 7.0) and Proteinase K 20 mg/ml. The total volume of lysis buffer and the Proteinase K in the kit could be 110 mL with $^{95}/_{100}$ parts lysis buffer and $^{5}/_{100}$ parts Proteinase K. When extracting DNA and RNA from a sample 800 µL of lysis buffer and 40 µL of Proteinase K are added per extraction sample. The wash buffer, preferably 10 mM TrisHCl (pH 6.5) can be provided at a volume of 265 mL and wash buffer with DNase could be provided at a total volume of 75 ML and $^{98}/_{100}$ parts of the wash buffer, $^{1}/_{100}$ part of DNase at 1 U/µL and $^{1}/_{100}$ part of DNase buffer. The kit preferably also comprises an elution buffer, such as 10 mM TrisHCl, 1 mM EDTA (pH 8.6) at a volume of 100 mL.

The present invention can also be used to purify nucleotide species from fresh and frozen mammalian organs and blood. The isolation of nucleotide species may be from prokaryotes, eukaryotes, and mitochondria.

With minor modifications in pre-treatment, the invention can be used to purify nucleotide species from formaldehyde-fixed paraffin-embedded tissues and plant tissues.

With addition of acetone to the lysis buffer, the recovery of low molecular weight RNA species might be enhanced.

The following, non-limiting examples teach various embodiments of the invention.

EXAMPLES

Example 1

Magnetic or Superparamagnetic Silicaceous Supports were Evaluated for Their Ability to Bind and Release High Quality DNA from a Complex Tissue Lysate Three 10 μm thick OCT embedded frozen tissue sections from breast, colon, spleen, and tonsil or frozen white blood cell pellets ($3 \times 10^6$ cells) were homogenized in 1 ml Lysis Buffer (7 M Guanidine HCl, 50 mM Tris pH 7, 4 U Proteinase K (Roche), 2% Tween 20) by grinding with a 3 mm steel ball for 15 min at 55° C. under rotary shaking at 800 rpm. To 200 μL lysate, 0.5 mg of MagPrep Silica HS particles (Merck) was added to capture DNA. For the DNA-binding screen, 0.5 mg of each bead [MagPrep Silica HS (Merck), SiMag (Chemicell), Magnesil (Promega), MagsiDNA (Magnamedics), S1.0 and S1.0-COOH (Mobitec) and Accubead (Bioneer)] were used. Beads were recovered using a magnet for one min and washed 3 times for 1 min in 150 μL Wash Buffer (10 mM Tris-HCl pH 6.5). DNA was eluted from the beads by addition of 200 μL Elution Buffer (10 mM Tris-HCl pH 9, 1 mM EDTA), mixing 20 times and heating to 65° C. for 5 min. Sample matched control DNA was extracted from OCT embedded frozen tissue by overnight Proteinase K digestion followed by phenol chloroform extraction and ethanol precipitation.

Real time PCR quantification of the human LINE1 repeat element was carried out using SYBR Green I (Biochemika) detection and forward primer 5'-AAAGCCGCTCAACTA-CATGG-3' (SEQ ID NO. 1) and reverse primer 5'-TGCTTTGAATGCGTCCCAGAG-3' (SEQ ID NO. 2) on an 7900 HT Fast Real Time PCR system (Applied Biosystems, Foster City, Calif., USA). Thermocycling parameters were 94° C. for 1 min, followed by 35 cycles of 94° C. for 10 seconds, 58° C. for 15 seconds and 70° C. for 15 seconds. Results from the bead screen are shown in FIG. 2A.

Figure 2:
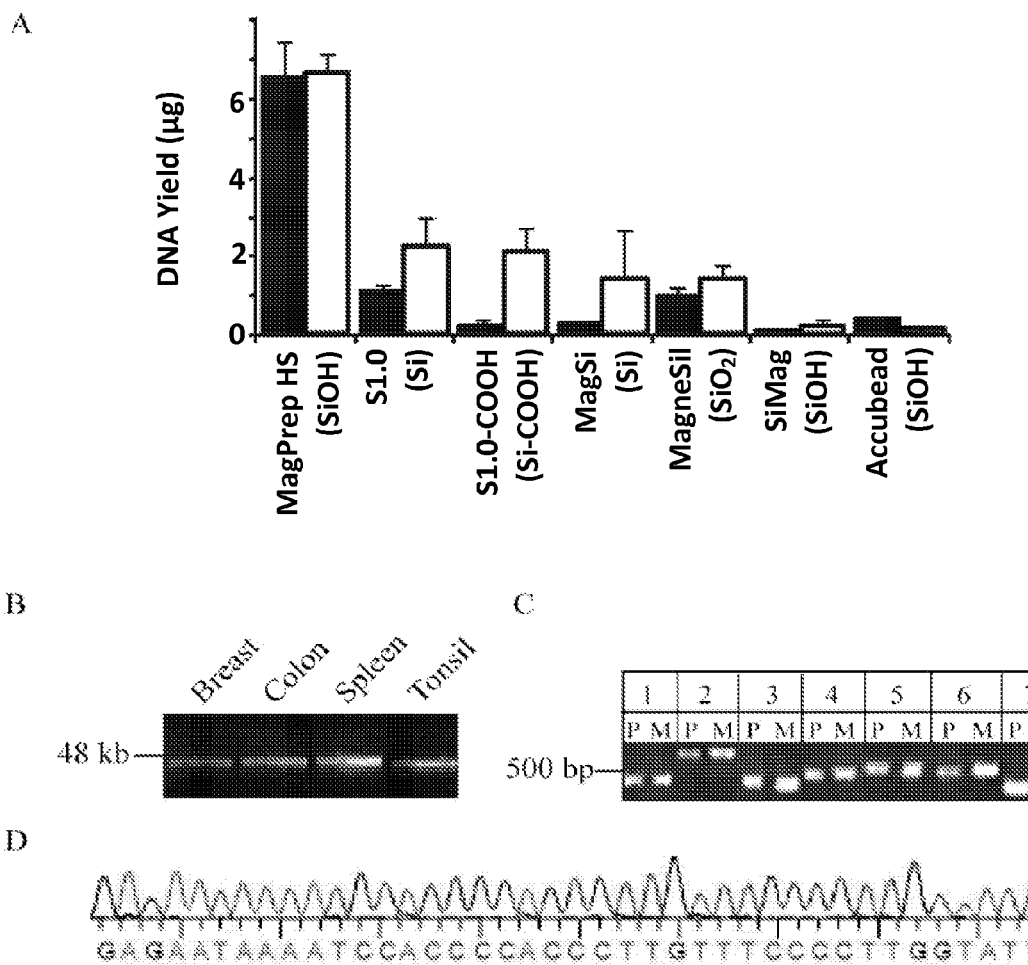
FIG. 2 presents data to support recovery of high quality genomic DNA from frozen tissue samples using MagPrep HS magnetic silica particles. A. DNA recovery from lysates of 3×10 µM of OCT embedded frozen spleen employing different silica beads was quantified by spectrophotometry (open bars) and real time PCR amplification of LINE1 elements (closed bars). Mean and SD of 3 independent experiments. B. Fragment length of DNA extracted from breast cancer, colon, spleen, and tonsil using MagPrep HS particles. C. PCR amplification of protein encoding exons of PRPS1. The 7 protein-encoding exons of PRPS1 were amplified by PCR in genomic DNA obtained from colon tissue by phenol-chloroform extraction (P), and in genomic DNA obtained from colon using MagPrep HS particles (M). D. Capillary sequencing traces of PRPS1 exon 7 in genomic DNA obtained from colon using MagPrep HS particles.

Assessment of DNA fragment length was performed by electrophoretic separation in a 0.4% agarose gel with a High Range DNA ladder (Fermentas) as size standard (FIG. 2B). PCR amplification and sequencing of exons 1 to 7 of the PRPS1 gene was carried out using 6 ng of gDNA as template. All primers were synthesized by Sigma (Table 1). PCR was performed in 10 μl reactions containing 10×PCR Buffer (166 mM $NH_4SO_4$, 670 mM Tris, pH 8.8, 67 mM $MgCl_2$, 100 mM 2-mercaptoethanol), 10 mM dNTPs (Invitrogen), 10 μM forward and reverse primers, 6% DMSO, 0.5 U Platinum Taq (Invitrogen) and 6 ng DNA. Reactions were carried out in a 2720 Thermal Cycler (Applied Biosystems) using a touch-down PCR protocol with hotstart (96° C. for 2 min; 3 cycles of 96° C. for 10 s, 64° C. for 10 s, 70° C. for 30 s; 3 cycles of 96° C. for 10 s, 61° C. for 10 s, 70° C. for 30 s; 3 cycles of 96° C. for 10 s, 58° C. for 10 s, 70° C. for 30 s; 41 cycles of 96° C. for 10 s, 57° C. for 10 s, 70° C. for 30 s; 1 cycle of 70° C. for 5 min).

TABLE 1

PRPS1 primers

| Primer | Sequence | SEQ ID NO. |
|---|---|---|
| Exon 1 M13F | 5'-gtaaaacgacggccagtcgcttggtattgagtctgtgg-3' | 3 |
| Exon 1 R | 5'-gctagtcacagagctgcaccc-3' | 4 |
| Exon 2 M13F | 5'-gtaaaacgacggccagtacctatggatatggagggctg-3' | 5 |
| Exon 2 R | 5'-actccagaggagttggtgctt-3' | 6 |
| Exon 3 M13F | 5'-gtaaaacgacggccagttgtctccttctatgaatttctggg-3' | 7 |
| Exon 3 R | 5'-cttctctgcagtcttcagcatc-3' | 8 |
| Exon 4 F | 5'-tcccatcagtttgaatgttgc-3' | 9 |
| Exon 4 M13R | 5'-gtaaaacgacggccagtcccatgtgctagctacttacatcc-3' | 10 |
| Exon 5 F | 5'-cctgaccttgtgatccgc-3' | 11 |
| Exon 5 M13R | 5'-gtaaaacgacggccagttcagcaggctgaagacattc-3' | 12 |
| Exon 6 F | 5'-tgttgtggaagcctaagcagg-3' | 13 |
| Exon 6 M13R | 5'-gtaaaacgacggccagtgatgacaagactaaatccttcagacc-3' | 14 |
| Exon 7 M13F | 5'-gtaaaacgacggccagtcatgacagggaaacagcacag-3' | 15 |
| Exon 7 R | 5'-cgggtcttctgctgaatttg-3' | 16 |

Agarose gel separation of PCR products is shown in FIG. 2C.

Templates were purified by solid phase reversible immobilization (SPRI) and sequencing was carried out with M13 forward primer (5'-GTAAAACGACGGCCAGT-3', SEQ ID NO. 17) and Big Dye Terminator Kit (Applied Biosystems) using conventional Sanger sequencing (FIG. 2D).

Example 2

Figure 3:
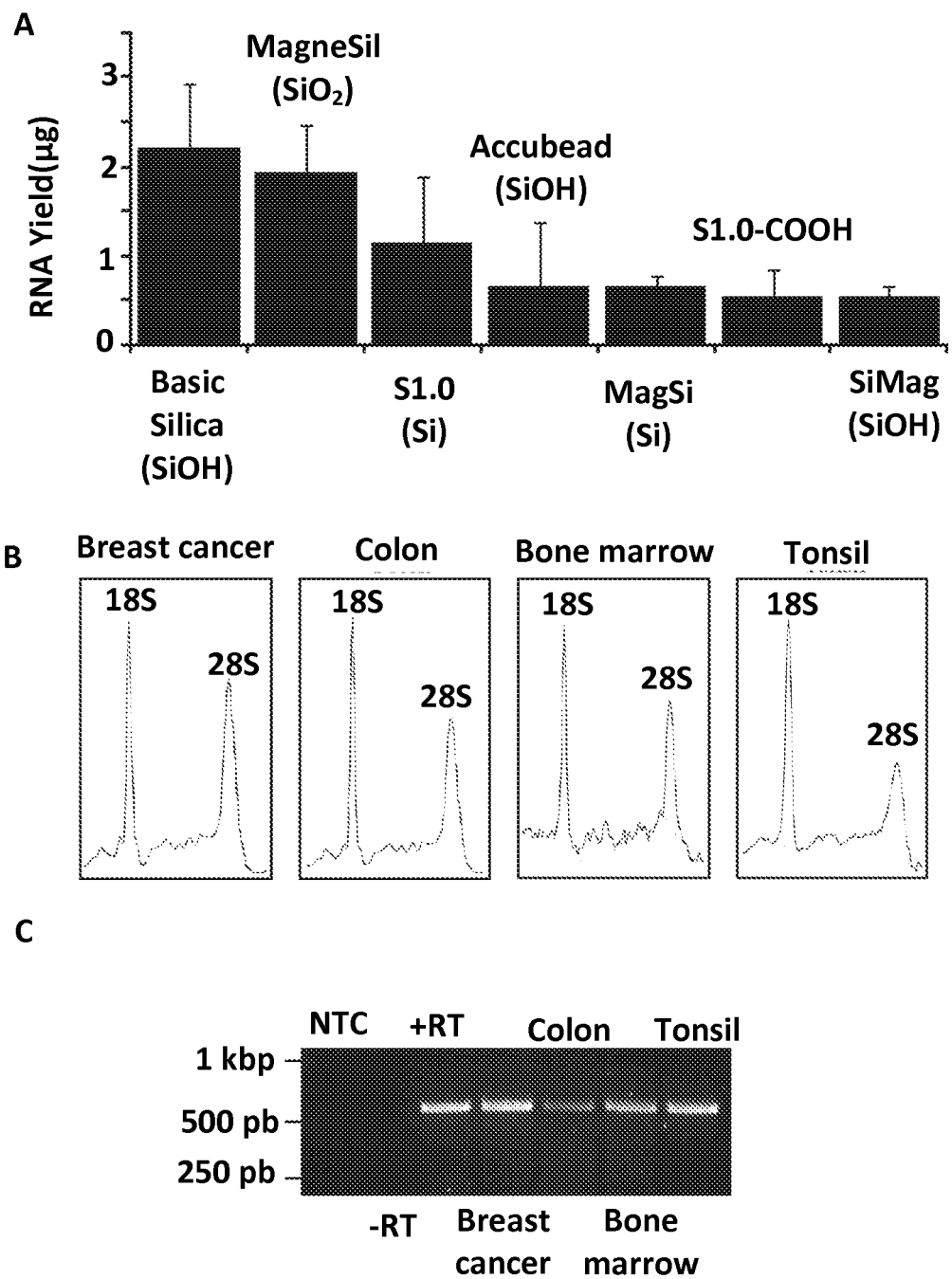
FIG. 3 presents data to support recovery of high quality total RNA from tissue lysates after DNA recovery. A. Total RNA yields after binding of total RNA from frozen tonsil tissue to silicaceous beads of different types, followed by washing and elution. Mean and SD of 3 experiments. B. Electrophoretic separation of total RNA samples extracted from breast cancer, colon, bone marrow and tonsil. C. Reverse transcription-coupled PCR amplification of ACTB in serially purified RNA from lysates of breast cancer, colon, frozen bone marrow cell pellets and tonsil. NTC, non-template control; –RT, no reverse transcriptase; +RT, positive control.

Magnetic or Superparamagnetic Silicaceous Supports were Evaluated for their Ability to Bind and Release High Quality RNA from a Complex Tissue Lysate Three 10 µm thick OCT embedded frozen tissue sections from breast, colon, spleen, and tonsil or frozen white blood cell pellets ($3 \times 10^6$ cells) were homogenized in 1 ml Lysis Buffer (7 M Guanidine HCl, 50 mM Tris pH 7, 4 U Proteinase K (Roche), 2% Tween 20) by grinding with a 3 mm steel ball for 15 min at 55° C. under rotary shaking at 800 rpm. To 200 µL lysate, 0.5 mg of MagPrep Silica HS particles (Merck) was added to capture DNA. The particles were recovered using a magnet for one min and washed 3 times for 1 min in 150 µL Wash Buffer (10 mM Tris-HCl pH 6.5). DNA was eluted from the beads by addition of 200 µL Elution Buffer (10 mM Tris-HCl pH 9, 1 mM EDTA), mixing 20 times and heating to 65° C. for 5 min. For the RNA-binding screen, 0.5 mg of each bead [MagPrep Basic Silica (Merck), SiMag (Chemicell), Magnesil (Promega), MagsiDNA (Magnamedics), S1.0 and S1.0-COOH (Mobitec) and Accubead (Bioneer)] were added to the supernatant post DNA recovery, followed by mixing 5 times and incubation for 15 min. Beads were recovered using a magnet for one min and washed in Wash Buffer for 1 min, Wash Buffer with 2U DNase I (Fermentas) for 15 min at 37° C., and in Wash Buffer for 1 min. Total RNA was eluted from the MagPrep beads by addition of 100 µL Elution Buffer, mixing 20 times and incubation for 5 min on ice. Results of the bead screen are illustrated in FIG. 3A. RNA integrity and concentration was determined in a Bioanalyzer instrument (Agilent) using an RNA 6000 Nano kit (FIG. 3B). 5 ng of RNA was reverse transcribed to cDNA and used to PCR amplify ACTB. cDNA was synthesized according to manufacturer's instructions by reverse transcription using Access-Quick™ RT-PCR System (Promega) and used in a touch-down PCR protocol (as described above) with forward and reverse ACTB primers 5'-CTGGGACGACATG-GAGAAAA-3' (SEQ ID NO. 18) and 5'-AAGGAAGGCTG-GAAGAGTGC-3' (SEQ ID NO. 19) respectively. Control RNA was extracted from blood using QIAamp RNA Blood Mini Kit from Qiagen according to manufacturer's instructions. The results are shown in FIG. 3C.

Example 3

Figure 4:
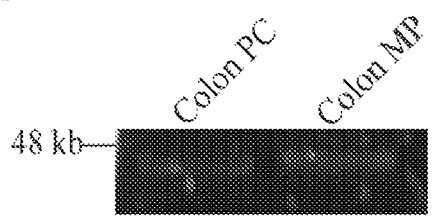
FIG. 4 Illustrates that DNA extracted by the method described can be compared with the integrity of DNA extracted by standard phenol/chloroform extraction. Also, the method describes results in elution of DNA with no RNA contamination. A. Electrophoretic sizing of gDNA from colon extracted by phenol chloroform protocol (PC) or extracted by the protocol outlined in FIG. 1 (MP); B. No RT PCR amplification of ACTB using DNA extracted from breast cancer, colon, spleen and tonsil, i.e. no RNA contamination in extracted DNA.
Figure 4:
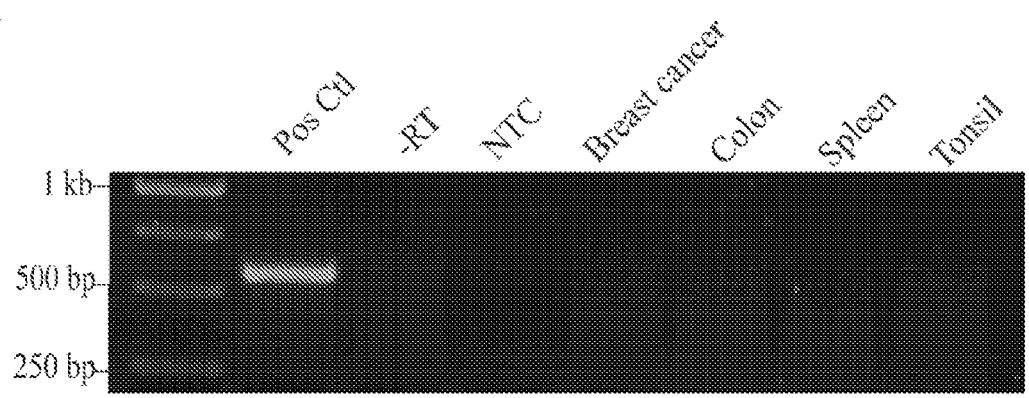

Using DNA extracted as described in Example 2, sizing by electrophoresis as outlined in Example 1 demonstrated that the recovered DNA fragments after MagPrep purification were up to 48 kb in length, similar to DNA from tissues extracted by phenol-chloroform (FIG. 4A). Also, no RNA contamination of the eluted DNA was observed in reverse transcription-PCR amplification of ACTB using eluted DNA as template (FIG. 4B).

Example 4

Figure 5:
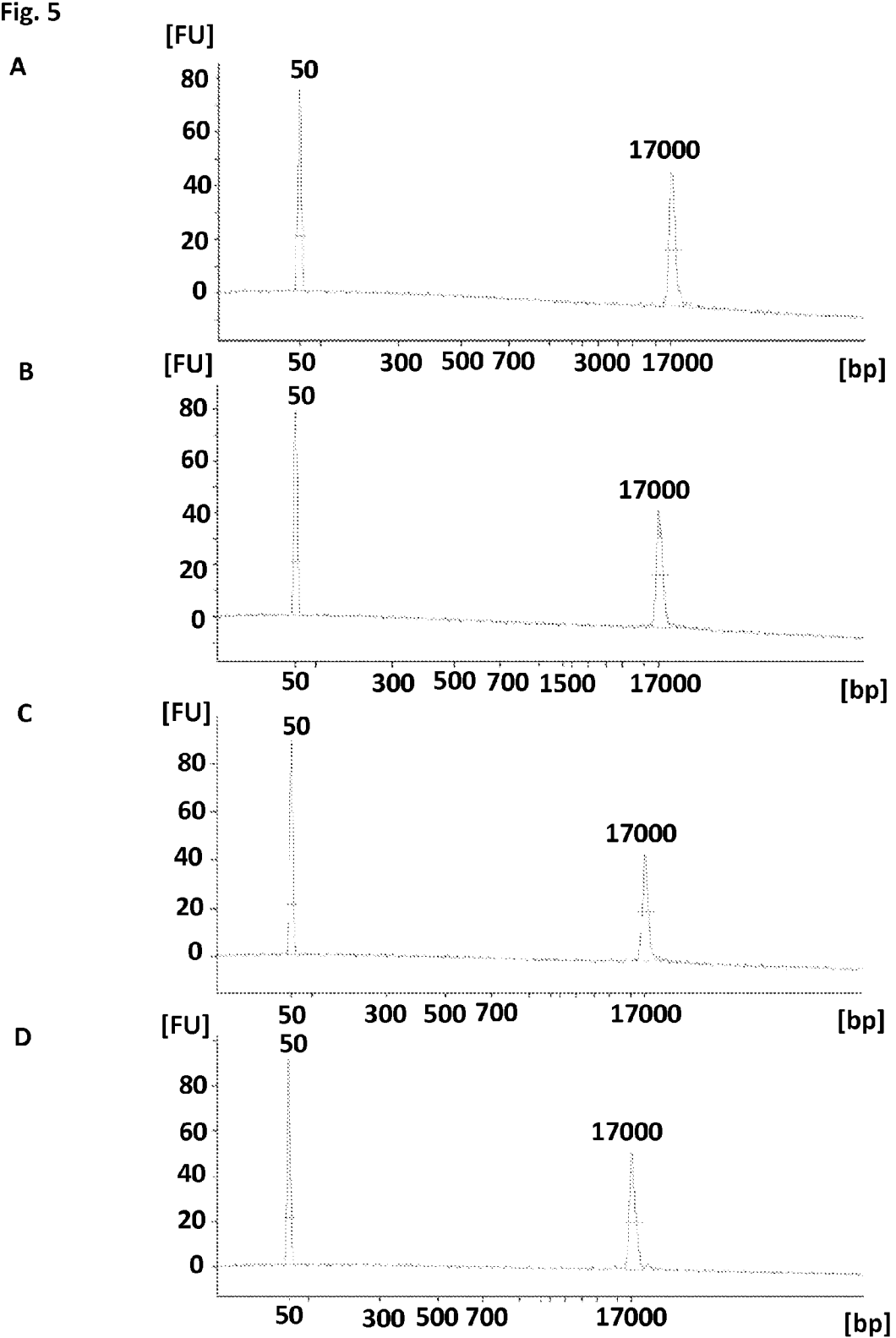
FIG. 5 Illustrates that gDNA contains no short fragments between 50 bp and 17 kbp (markers) as illustrated by DNA sizing on an Agilent Bioanalyzer. A. DNA from breast cancer tissue, B. DNA from colon tissue, C. DNA from spleen tissue, D. DNA from tonsil tissue.

Using DNA extracted as described in Example 2, sizing by electrophoresis on an Agilent Bioanalyzer showed that the DNA extracted was found to consist solely of long fragments (FIG. 5).

Example 5

Figure 6:
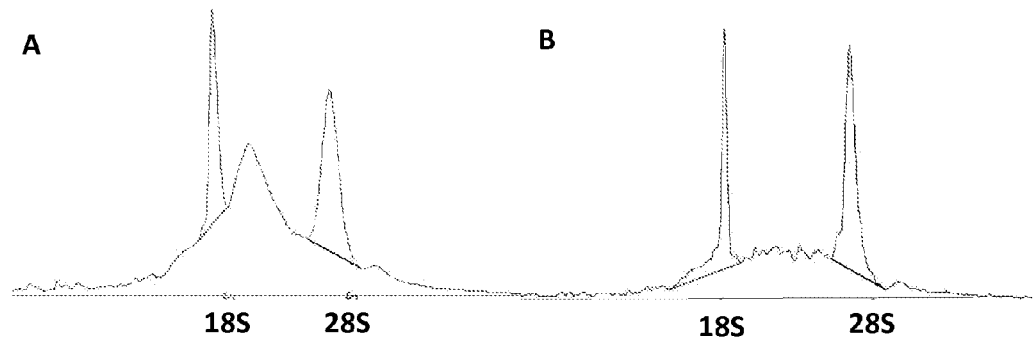
FIG. 6 supports the claim that the extraction of RNA as described in Example 2 does not affect sample integrity as shown by electrophoretic separation on an Agilent Bioanalyzer RNA gel. A. RNA input (RIN=7.1), B. RNA eluate (RIN=8.7).

The integrity of a control total RNA sample extracted using MagPrep Basic Silica particles as described in Example 2 was not affected by the procedure. Electrophoretic separation of a reference RNA sample before and after extraction by Basic MagPrep Silica beads demonstrates the integrity retention of RNA sample as illustrated in FIGS. 6A and 6B.

Example 6

Prior DNA Extraction Facilitates Higher RNA Recovery over a Range of DNA:RNA Input Ratios RNA was extracted from known mixtures of DNA and RNA (Table 2) by Basic Silica only and by Silica HS beads followed by Basic Silica as described in FIG. 1. RNA concentration was determined using an RNA Nano kit on the Bioanalyzer (Agilent). Percentage recovery is consistently higher upon removal of DNA prior to RNA extraction. RNA recovery is also greater with lower RNA input.

TABLE 2

Experimental conditions for RNA extractions 1 to 5

| Extraction | Input RNA (µg) | Input DNA (µg) |
|---|---|---|
| 1 | 2 | 8 |
| 2 | 2 | 4 |
| 3 | 2 | 2 |
| 4 | 4 | 2 |
| 5 | 8 | 2 |

Figure 7:
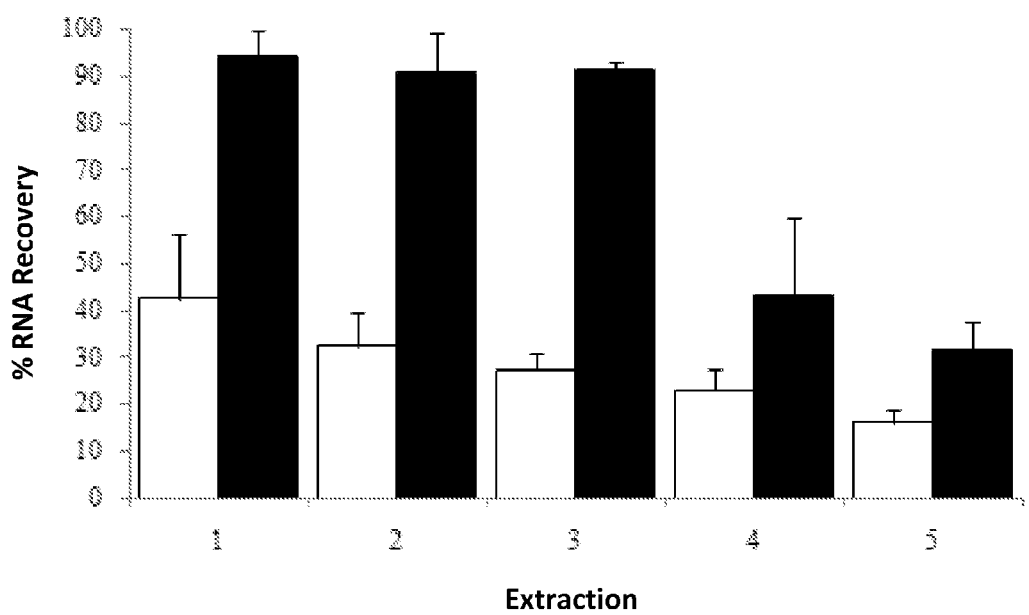
FIG. 7 presents a graph to support the claim that prior recovery of DNA facilitates RNA recovery. Percentage RNA recovery by MagPrep Basic Silica only is illustrated by open bars and percentage RNA recovery by MagPrep Silica HS beads followed by MagPrep Basic Silica is illustrated by closed bars.

The results are shown in FIG. 7. Open bars, MagPrep Basic Silica; Closed bars, MagPrep Silica HS followed by MagPrep Basic Silica.

Example 7

Figure 8:
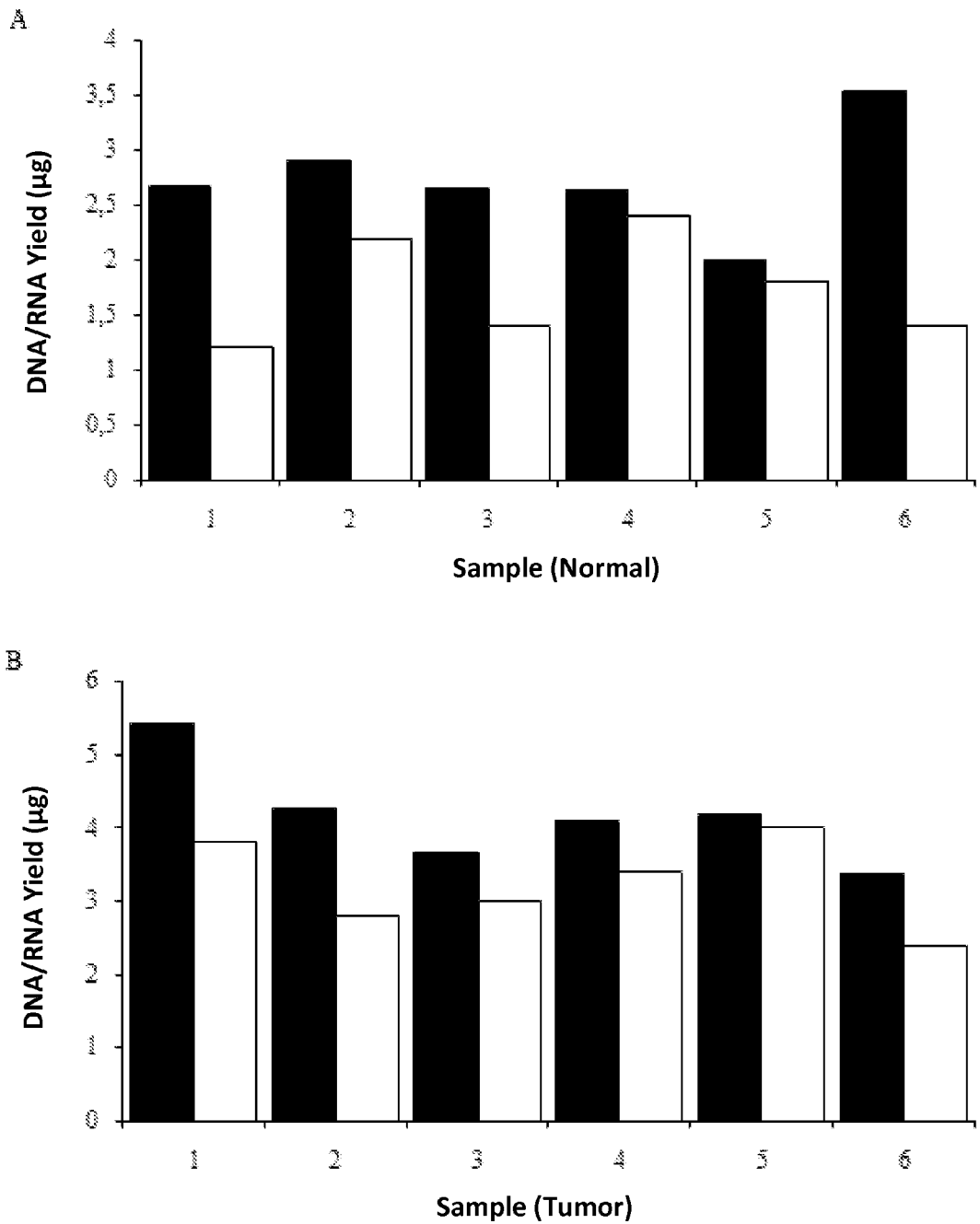
FIG. 8 illustrates the application of sequential DNA and RNA extraction (as described) to patient matched tumor and normal colon tissue samples. A. Total DNA (closed bars) and RNA (open bars) yields from six patient matched normal colon tissue samples, B. Total DNA (closed bars) and RNA (open bars) yields from six patient matched tumor colon tissue samples.

Sequential DNA/RNA Extraction from Patient Matched Normal and Tumor Colon Samples Three 10 µm thick OCT embedded frozen tissue sections from 12 patient matched tumor/normal colon were homogenized in 1 ml Lysis Buffer (7 M guanidine HCl, 50 mM Tris pH 7, 4 U Proteinase K (Roche), 2% Tween-20) by grinding with a 3 mm steel ball for 15 min at 55° C. under rotary shaking at 800 rpm. To 200 µL lysate, 0.5 mg of MagPrep Silica HS particles (Merck) was added to capture DNA. Beads were recovered using a magnet for one min and washed 3 times for 1 min in 100 µL Wash Buffer (10 mM Tris-HCl pH 6.5). DNA was eluted from the beads by addition of 100 µL Elution Buffer (10 mM Tris-HCl pH 9, 1 mM EDTA), mixing 20 times and heating to 65° C. for 5 min. To the supernatant post DNA recovery, 0.5 mg MagPrep Basic Silica beads was added, followed by mixing 5 times and incubation for 15 min. Beads were recovered using a magnet for one min and washed in 100 µL ice cold Wash Buffer for 1 min, Wash Buffer with 2 U DNase I (Fermentas) for 15 min at 37° C., and in ice cold Wash Buffer for 1 min. Total RNA was eluted from the Mag- Prep beads by addition of 50 μL Elution Buffer, mixing 20 times and incubation for 5 min at 65° C. The concentration of DNA extracted from the 6 normal tissues was measured spectrophotmetrically on a Nanodrop while the concentration of RNA was measured using an RNA Nano kit on the Bioanalyzer (Agilent). The yields are illustrated in FIG. 8A. Open bars, DNA; closed bars; RNA. The same measurements were taken for the tumor samples and the yields obtained are illustrated in FIG. 8B. Open bars, DNA; closed bars; RNA.

Comparative Example 1

An Organic Solvent Added in the Wash Buffer

DNA was extracted using the protocol as described in Example 2 but using 70% v/v ethanol as wash buffer in parallel with the wash buffer as described by the present invention. This example was included to illustrate that organic solvents are not required in the wash step. The results are illustrated in Table 3.

TABLE 3

The effect of a different wash buffer on DNA concentration and purity

| Wash buffer | DNA conc. (ng/μl) | 260:280 ratio | 260:230 ratio |
|---|---|---|---|
| 70% v/v ethanol | 26.19 | 1.81 | 0.82 |
| 10 mM TrisHCl, pH 6.5 | 35.49 | 1.63 | 0.92 |

Thus, inclusion of an organic solvent in the form of 70% ethanol in the wash buffer actually reduced the yield and resulted in no improvement in 260:230 ratio as compared to a wash buffer according to the embodiments.

Comparative Example 2

Different Lysis/Binding Buffers

DNA and RNA were extracted from colon tissue as previously described herein but with the following lysis/binding buffers replacing the lysis buffer as described in Example 2. The lysis buffer according to the present embodiments was also included as a control.
(i) TAAN lysis buffer: 0.3 M ammonium sulfate in 99.2 mL of 0.2 mol/L Tris acetate, pH 4.0, 0.8% Nonidet P40
(ii) 3 M guanidium thiocyanate, 20 mM trisodium citrate
(iii) 41.1% v/v ethanol, 2 M guanidium thiocyanate, 14.4 mM trisodium citrate
(iv) 71.5% v/v isopropanol, 1 M guanidium thiocyanate, 7.2 mM triodium citrate
(v) 42.8% v/v methanol, 2 M guanidium thiocyante, 14.4 mM trisodium citrate
(vi) 6 M guanidium hydrochloride
(vii) 41.1% v/v ethanol, 4.1 M guanidium hydrochloride The purity and integrity of extracted biomolecules was assessed spectrophotometrically and by electrophoresis. The results are outlined in Table 4. It is evident that the purity and integrity of the nucleic acids is best maintained when using the lysis buffer of the present embodiments.

TABLE 4

The effect of different lysis buffer (LB)/binding buffer (BB) on nucleic acid integrity

| LB/BB | DNA Conc (ng/μl) | 260:280 | DNA Degradation | RNA Conc (ng/μl) | RNA Degradation |
|---|---|---|---|---|---|
| LB according to present invention | 51.73 | 1.65 | No | 5 | No |
| TAAN buffer | 39.79 | 1.56 | Yes | 0 | N/A |
| 3M GTC, 20 mM trisodium citrate | 57.4 | 3.31 | Yes | 4.4 | Yes |
| 41.1% v/v ETOH, 2M guanidium thiocyanate, 14.4 mM trisodium citrate | 33.8 | 3.64 | Yes | 0.3 | N/A |
| 71.5% v/v isopropanol, 1M GTC, 7.2 mM triodium citrate | 45.8 | 2.52 | Yes | 0.2 | N/A |
| 42.8% v/v MTOH, 2M guanidium thiocyante, 14.4 mM trisodium citrate | 62.9 | 2.79 | Yes | 3.8 | Yes |
| 6M GdnHCl | 33 | 1.7 | Yes | 5.5 | Some |
| 41.1% v/v ETOH, 4.1M GdnHCl | 37.1 | 1.65 | Yes | 4.5 | Some |

The LB buffer of the embodiments therefore results in high yield but without any degradation of the recovered DNA and RNA. The other tested buffers either resulted in lower yields and/or showed degradation of the recovered DNA and/or RNA.

The embodiments described above are to be understood as a few illustrative examples of the present invention. It will be understood by those skilled in the art that various modifications, combinations and changes may be made to the embodiments without departing from the scope of the present invention. In particular, different part solutions in the different embodiments can be combined in other configurations, where technically possible. The scope of the present invention is, however, defined by the appended claims.

The invention claimed is:

1. A method of serial recovery of two different nucleic acid species from a biological sample, comprising:

in a first binding step, homogenizing and enzymatically digesting the biological sample in a combined lysis and nucleic acid binding buffer, thereby generating a lysate comprising a first nucleic acid species and a second nucleic acid species, followed by selectively binding the first nucleic acid species to a first solid phase by contacting the lysate in the combined lysis and nucleic acid binding buffer with the first solid phase that selectively binds the first nucleic acid species;

separating the first solid phase with the bound first nucleic acid species from an unbound portion of the lysate;

in a second binding step, binding the second nucleic acid species to a second solid phase, different from the first solid phase, by contacting an unbound portion of the lysate in the combined lysis and nucleic acid binding buffer with the second solid phase that binds the first and second nucleic acid species;

enzymatically digesting the first nucleic acid species bound to the second solid phase; and isolating the second nucleic acid species from the second solid phase.

2. The method according to claim 1, wherein the combined lysis and nucleic acid binding buffer comprises a chaotropic salt solution or mildly acidic buffer.

3. The method according to claim 2, wherein the chaotropic salt solution is guanidine HCl.

4. The method according to claim 2, wherein the combined lysis and nucleic acid binding buffer comprises Proteinase K.

5. The method according to claim 1, wherein the combined lysis and nucleic acid binding buffer is devoid of alcohols.

6. The method according to claim 1, wherein the first nucleic acid species is deoxyribonucleic acid, DNA, and the second nucleic acid species is ribonucleic acid, RNA.

7. The method according to claim 1, wherein the first solid support preferentially binds DNA over RNA when contacted with a mixture containing DNA and RNA.

8. The method according to claim 1, wherein the second solid support binds RNA better than, or equally well as, DNA when contacted with a mixture containing DNA and RNA.

9. The method according to claim 1, wherein the first and/or second solid support is composed of magnetic or superparamagnetic particles.

10. The method according to claim 1, wherein the first and/or second solid support is composed of SiOH-coated magnetite crystals with >90% magnetite content in the size range 100-200 nm.

11. The method according to claim 1, wherein the separated first nucleic acid species is:

washed in a slightly acidic buffer; and eluted from the first solid support in a basic elution buffer.

12. The method according to claim 1, wherein the separated second nucleic acid is:

washed in a slightly acidic buffer; and eluted from the second solid support in a basic elution buffer.

13. The method according to claim 11, wherein the basic elution buffer is devoid of alcohols.

14. The method according to claim 12, wherein the washing buffer in the washing step for the second nucleic acid comprises DNase I.

15. The method according to claim 11, wherein the washing buffer is devoid of alcohols.

16. A kit for use in a method for serial recovery of two different nucleic acid species from a biological sample, the kit comprising a combined lysis and nucleic acid binding buffer, a first solid phase that selectively binds a first nucleic acid species in the combined lysis and nucleic acid binding buffer, and a second solid phase that is different from the first solid phase and binds a second nucleic acid species and the first nucleic acid species in the combined lysis and nucleic acid binding buffer.

17. The kit according to claim 16, wherein the combined lysis and nucleic acid binding buffer is devoid of alcohols.

18. The kit according to claim 16, wherein the combined lysis and nucleic acid binding buffer is an aqueous solution of 7 M guanidine HCl, 50 mM Tris pH 7, 2% Tween 20.

19. The kit according to claim 16, further comprising a wash buffer, a wash buffer for digestion of the first nucleic acid species, and an elution buffer.

20. The kit according to claim 19, wherein the wash buffer, the wash buffer for digestion of the first nucleic acid species, and the elution buffer are devoid of alcohols.

21. The kit according to claim 19, wherein the wash buffer is an aqueous solution of 10 mM Tris-HCl pH 6.5.

22. The kit according to claim 19, wherein the wash buffer for digestion of the first nucleic acid species is an aqueous solution of 10 mM Tris-HCl pH 6-7 and 1-2 U DNase I.

23. The kit according to claim 19, wherein the elution buffer is an aqueous solution of 10 mM Tris-HCl pH 8-10, and 1 mM EDTA.

24. The kit according to claim 16, wherein the first and/or second solid support is composed of SiOH-coated magnetite crystals with >90% magnetite content in the size range 100-200 nm.

25. The kit according to claim 16, where the first solid support preferentially binds DNA over RNA when contacted with a mixture of DNA and RNA.

26. The kit according to claim 16, where the second solid support binds RNA better than, or equally well as, DNA when contacted with a mixture containing DNA and RNA.

27. The method according to claim 2, wherein the combined lysis and nucleic acid binding buffer is devoid of alcohols.

28. The method according to claim 12, wherein the basic elution buffer is devoid of alcohols.

29. The method according to claim 12, wherein the washing buffer is devoid of alcohols.

30. The kit according to claim 22, wherein the wash buffer for digestion of the first nucleic acid species is an aqueous solution of 10 mM Tris-HCl pH 6.5 and 1 U DNase I.

31. The kit according to claim 23, wherein the elution buffer is an aqueous solution of 10 mM Tris-HCl pH 8.6 and 1 mM EDTA.

* * * * *

SEQUENCE LISTING

<160> NUMBER OF SEQ ID NOS: 19

<210> SEQ ID NO 1
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA"
      /organism="Homo sapiens"

<400> SEQUENCE: 1
aaagccgctc aactacatgg                                              20

```
<210> SEQ ID NO 2
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA"
      /organism="Homo sapiens"

<400> SEQUENCE: 2
tgctttgaat gcgtcccaga g                                              21

<210> SEQ ID NO 3
<211> LENGTH: 38
<212> TYPE: DNA
<213> ORGANISM: Homo sapiens
<220> FEATURE:
<221> NAME/KEY: source
<222> LOCATION: (1)..(38)
<223> OTHER INFORMATION: /mol_type="DNA"
      /organism="Homo sapiens"

<400> SEQUENCE: 3
gtaaaacgac ggccagtcgc ttggtattga gtctgtgg                             38

<210> SEQ ID NO 4
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA"
      /organism="Homo sapiens"

<400> SEQUENCE: 4
gctagtcaca gagctgcacc c                                              21

<210> SEQ ID NO 5
<211> LENGTH: 38
<212> TYPE: DNA
<213> ORGANISM: Homo sapiens
<220> FEATURE:
<221> NAME/KEY: source
<222> LOCATION: (1)..(38)
<223> OTHER INFORMATION: /mol_type="DNA"
      /organism="Homo sapiens"

<400> SEQUENCE: 5
gtaaaacgac ggccagtacc tatggatatg gagggctg                             38

<210> SEQ ID NO 6
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA"
      /organism="Homo sapiens"

<400> SEQUENCE: 6
actccagagg agttggtgct t                                              21

<210> SEQ ID NO 7
<211> LENGTH: 41
```

-continued

```
<212> TYPE: DNA
<213> ORGANISM: Homo sapiens
<220> FEATURE:
<221> NAME/KEY: source
<222> LOCATION: (1)..(41)
<223> OTHER INFORMATION: /mol_type="DNA"
      /organism="Homo sapiens"

<400> SEQUENCE: 7
gtaaaacgac ggccagttgt ctccttctat gaatttctgg g                          41

<210> SEQ ID NO 8
<211> LENGTH: 22
<212> TYPE: DNA
<213> ORGANISM: Homo sapiens
<220> FEATURE:
<221> NAME/KEY: source
<222> LOCATION: (1)..(22)
<223> OTHER INFORMATION: /mol_type="DNA"
      /organism="Homo sapiens"

<400> SEQUENCE: 8
cttctctgca gtcttcagca tc                                               22

<210> SEQ ID NO 9
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA"
      /organism="Homo sapiens"

<400> SEQUENCE: 9
tcccatcagt ttgaatgttg c                                                21

<210> SEQ ID NO 10
<211> LENGTH: 41
<212> TYPE: DNA
<213> ORGANISM: Homo sapiens
<220> FEATURE:
<221> NAME/KEY: source
<222> LOCATION: (1)..(41)
<223> OTHER INFORMATION: /mol_type="DNA"
      /organism="Homo sapiens"

<400> SEQUENCE: 10
gtaaaacgac ggccagtccc atgtgctagc tacttacatc c                          41

<210> SEQ ID NO 11
<211> LENGTH: 18
<212> TYPE: DNA
<213> ORGANISM: Homo sapiens
<220> FEATURE:
<221> NAME/KEY: source
<222> LOCATION: (1)..(18)
<223> OTHER INFORMATION: /mol_type="DNA"
      /organism="Homo sapiens"

<400> SEQUENCE: 11
cctgaccttg tgatccgc                                                    18

<210> SEQ ID NO 12
<211> LENGTH: 37
<212> TYPE: DNA
<213> ORGANISM: Homo sapiens
<220> FEATURE:
<221> NAME/KEY: source
```

```
<222> LOCATION: (1)..(37)
<223> OTHER INFORMATION: /mol_type="DNA"
      /organism="Homo sapiens"

<400> SEQUENCE: 12
gtaaaacgac ggccagttca gcaggctgaa gacattc                       37

<210> SEQ ID NO 13
<211> LENGTH: 21
<212> TYPE: DNA
<213> ORGANISM: Homo sapiens
<220> FEATURE:
<221> NAME/KEY: source
<222> LOCATION: (1)..(21)
<223> OTHER INFORMATION: /mol_type="DNA"
      /organism="Homo sapiens"

<400> SEQUENCE: 13
tgttgtggaa gcctaagcag g                                        21

<210> SEQ ID NO 14
<211> LENGTH: 43
<212> TYPE: DNA
<213> ORGANISM: Homo sapiens
<220> FEATURE:
<221> NAME/KEY: source
<222> LOCATION: (1)..(43)
<223> OTHER INFORMATION: /mol_type="DNA"
      /organism="Homo sapiens"

<400> SEQUENCE: 14
gtaaaacgac ggccagtgat gacaagacta aatccttcag acc                43

<210> SEQ ID NO 15
<211> LENGTH: 38
<212> TYPE: DNA
<213> ORGANISM: Homo sapiens
<220> FEATURE:
<221> NAME/KEY: source
<222> LOCATION: (1)..(38)
<223> OTHER INFORMATION: /mol_type="DNA"
      /organism="Homo sapiens"

<400> SEQUENCE: 15
gtaaaacgac ggccagtcat gacagggaaa cagcacag                      38

<210> SEQ ID NO 16
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA"
      /organism="Homo sapiens"

<400> SEQUENCE: 16
cgggtcttct gctgaatttg                                          20

<210> SEQ ID NO 17
<211> LENGTH: 17
<212> TYPE: DNA
<213> ORGANISM: Homo sapiens
<220> FEATURE:
<221> NAME/KEY: source
<222> LOCATION: (1)..(17)
<223> OTHER INFORMATION: /mol_type="DNA"
      /organism="Homo sapiens"
```

```
<400> SEQUENCE: 17
gtaaaacgac ggccagt                                                    17

<210> SEQ ID NO 18
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA"
      /organism="Homo sapiens"

<400> SEQUENCE: 18
ctgggacgac atggagaaaa                                                 20

<210> SEQ ID NO 19
<211> LENGTH: 20
<212> TYPE: DNA
<213> ORGANISM: Homo sapiens
<220> FEATURE:
<221> NAME/KEY: source
<222> LOCATION: (1)..(20)
<223> OTHER INFORMATION: /mol_type="DNA"
      /organism="Homo sapiens"

<400> SEQUENCE: 19
aaggaaggct ggaagagtgc                                                 20
```